United States Patent
Flagler et al.

(10) Patent No.: US 8,936,025 B2
(45) Date of Patent: Jan. 20, 2015

(54) TRACHEOSTOMY TUBE AND TECHNIQUE FOR USING THE SAME

(75) Inventors: Robert W. Flagler, Pleasanton, CA (US); Carl Kling, San Ramon, CA (US); Michael H. Vardanega, Livermore, CA (US)

(73) Assignee: Covidien LP, Mansfield, MA (US)

( * ) Notice: Subject to any disclaimer, the term of this patent is extended or adjusted under 35 U.S.C. 154(b) by 1510 days.

(21) Appl. No.: 11/527,070

(22) Filed: Sep. 26, 2006

(65) Prior Publication Data

US 2008/0072911 A1      Mar. 27, 2008

(51) Int. Cl.
A61M 16/00      (2006.01)
A61B 9/00       (2006.01)
B29C 45/14      (2006.01)
A61M 16/04      (2006.01)
B29C 45/16      (2006.01)
A61M 16/08      (2006.01)
B29L 31/00      (2006.01)
B29L 23/00      (2006.01)

(52) U.S. Cl.
CPC ....... *A61M 16/0465* (2013.01); *A61M 16/0816* (2013.01); *B29C 45/14598* (2013.01); *B29C 45/1676* (2013.01); *B29L 2031/753* (2013.01); *A61M 16/0427* (2013.01); *A61M 16/0497* (2013.01); *A61M 16/0434* (2013.01); *B29L 2023/00* (2013.01)
USPC .............. 128/207.17; 128/207.14; 128/207.15

(58) Field of Classification Search
CPC .................... A61M 16/0816; A61M 16/0427; A61M 16/0497; A61M 16/0434; B29C 45/14598; B29C 45/1675; B29L 2031/753; B29L 2023/00

USPC ............ 128/207.17, 207.14, 207.15, 200.26, 128/912

See application file for complete search history.

(56) References Cited

U.S. PATENT DOCUMENTS

| 2,786,469 | A | | 3/1957 | Cohen |
| 3,169,529 | A | | 2/1965 | Koenig |
| 3,225,767 | A | | 12/1965 | Smith |
| 4,033,353 | A | | 7/1977 | La Rosa |
| 4,235,229 | A | * | 11/1980 | Ranford et al. .......... 128/207.17 |
| 4,315,505 | A | | 2/1982 | Crandall et al. |
| 4,332,245 | A | | 6/1982 | Boone, Sr. |

(Continued)

FOREIGN PATENT DOCUMENTS

DE      4100837        7/1992
DE      4100837 A1     7/1992

(Continued)

OTHER PUBLICATIONS

EP13005021.4 Notice of Publication mailed Jan. 7, 2014.

(Continued)

*Primary Examiner* — Justine Yu
*Assistant Examiner* — Michael Tsai
(74) *Attorney, Agent, or Firm* — Fletcher Yoder PC (57) ABSTRACT

A molded tracheostomy tube may provide enhanced comfort for a patient. A unitary molded coating over areas of the tracheostomy tube that come into contact with the patient's skin may prevent irritation. Further, the overmolding manufacturing process may allow the tracheostomy tube assembly to incorporate features that allow for greater ease of movement for a patient, such as features that allow flexing at the connection point of the tracheostomy tube to other medical devices.

34 Claims, 5 Drawing Sheets

(56) References Cited

U.S. PATENT DOCUMENTS

| | | | |
|---|---|---|---|
| 4,340,046 A * | 7/1982 | Cox | 128/207.17 |
| 4,449,523 A | 5/1984 | Szachowicz | |
| 4,573,460 A | 3/1986 | Szachowicz et al. | |
| 4,573,979 A | 3/1986 | Blake | |
| 4,955,861 A | 9/1990 | Enegren et al. | |
| 5,054,482 A | 10/1991 | Bales | |
| 5,390,669 A | 2/1995 | Stuart et al. | |
| 5,458,139 A | 10/1995 | Pearl | |
| 5,460,176 A | 10/1995 | Frigger | |
| 5,579,762 A | 12/1996 | Lee | |
| 5,645,048 A | 7/1997 | Brodsky et al. | |
| 5,697,365 A | 12/1997 | Pell | |
| 5,806,515 A * | 9/1998 | Bare et al. | 128/207.15 |
| 5,819,734 A * | 10/1998 | Deily et al. | 128/207.17 |
| 5,864,938 A | 2/1999 | Gansel et al. | |
| 6,135,110 A | 10/2000 | Roy | |
| 6,135,111 A * | 10/2000 | Mongeon | 128/207.15 |
| 6,248,099 B1 | 6/2001 | Bell | |
| 6,634,357 B1 | 10/2003 | Hamilton | |
| 6,698,424 B2 | 3/2004 | Madsen et al. | |
| 6,772,758 B2 | 8/2004 | Lambert | |
| 7,147,252 B2 | 12/2006 | Teuscher et al. | |
| 7,328,702 B2 | 2/2008 | Gostelow | |
| 2003/0158539 A1 | 8/2003 | Bouphavishith et al. | |
| 2005/0005941 A1 | 1/2005 | Bischoff | |
| 2005/0144761 A1 | 7/2005 | Hatcher | |
| 2005/0161047 A1 | 7/2005 | Briggs, III | |
| 2005/0166924 A1 * | 8/2005 | Thomas et al. | 128/207.14 |
| 2005/0188993 A1 | 9/2005 | Steeves et al. | |
| 2006/0060201 A1 | 3/2006 | Beagle et al. | |
| 2007/0144526 A1 | 6/2007 | Blom et al. | |
| 2008/0072911 A1 | 3/2008 | Flagler et al. | |
| 2008/0142003 A1 | 6/2008 | Depel | |
| 2009/0025730 A1 | 1/2009 | Pinel | |

FOREIGN PATENT DOCUMENTS

| | | |
|---|---|---|
| DE | 10140292 | 3/2003 |
| DE | 10140292 A1 | 3/2003 |
| EP | 2168256 A | 6/1986 |
| EP | 0227230 | 7/1987 |
| EP | 0227230 A1 | 7/1987 |
| EP | 1005877 A2 | 6/2000 |
| EP | 1 219 317 A | 7/2002 |
| GB | 2028139 | 3/1980 |
| GB | 2028139 A | 3/1980 |
| GB | 2 205 504 A | 12/1988 |
| GB | 2 328 878 A | 3/1999 |
| WO | 95033506 | 12/1995 |
| WO | WO 9533506 | 12/1995 |
| WO | 0204856 A1 | 1/2002 |
| WO | WO0204856 | 1/2002 |
| WO | WO 2007/008418 A | 1/2007 |

OTHER PUBLICATIONS

EP13005021.4 Extended Search Report mailed Jan. 8, 2014.

Arcadia Medical—Silicone Air Cuff Adjustable Neck Flange Tracheostomy Tubes, Pediatric & Neonatal TT, Adjustable Neck Flange TT (Apr. 1, 2010); http://www.arcadiamedical.com/arcadia/main.asp?cid=4&pid=2.

Bivona Adult Mid-Range Aire-Cuf Adjustable Neck Flange Hyperflex Trachheostomy Tubes (Apr. 1, 2010); http://www.smiths-medical.com/catalog/endotracheal-tubes.

Teleflex Medical—Rusch Rusch Adjustable Flange Pediatric (Mar. 31, 2010 and Apr. 1, 2010); http://www.teleflexmedical.com/prod_rusch.php.

Teleflex Medical—Rusch QuickTrach (Mar. 31, 2010 and Apr. 1, 2010); http://www.teleflexmedical.com/prod_rusch.php.

Teleflex Medical—RuschTrach Cap & Conn. Set (Mar. 31, 2010 and Apr. 1, 2010); http://www.teleflexmedical.com/prod_rusch.php.

Teleflex Medical—Rusch Trach Collar (Mar. 31, 2010 and Apr. 11, 2010); http://www.teleflexmedical.com/prod_rusch.php.

Tracoe medical GmBH—Vario (Apr. 1, 2010); http://www.tracoe.com/products.html.

Teleflex Medical—Rusch Tracheoflex (Mar. 1, 2010 and Apr. 1, 2010); http://www.teleflexmedical.com/prod_rusch.php.

Rusch PercuQuick Trach Set (Mar. 1, 2010 and Apr. 1, 2010); http://www.teleflexmedical.com/prod_rusch.php.

* cited by examiner

TRACHEOSTOMY TUBE AND TECHNIQUE FOR USING THE SAME

BACKGROUND OF THE INVENTION

1. Field of the Invention

The present invention relates to medical devices, and more particularly, to airway devices, such as tracheostomy tubes.

2. Description of the Related Art

This section is intended to introduce the reader to various aspects of art that may be related to various aspects of the present invention which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the course of treating a patient, a tube or other medical device may be used to control the flow of air, food, fluids, or other substances into the patient. For example, medical devices, such as tracheal tubes, may be used to control the flow of one or more substances into or out of a patient. In many instances, it is desirable to provide a seal between the outside of the tube or device and the interior of the passage in which the tube or device is inserted. In this way, substances can only flow through the passage via the tube or other medical device, allowing a medical practitioner to maintain control over the type and amount of substances flowing into and out of the patient.

More specifically, tracheal tubes may be used to control the flow of air or other gases through a patient's trachea. Such tracheal tubes may include endotracheal tubes or tracheostomy tubes. While patients may be intubated using endotracheal tubes during emergencies or shorter hospital stays, tracheostomy tubes are more typically used for prolonged ventilation, as the use of a tracheostomy tube is generally more comfortable for a patient.

A typical tracheostomy tube is generally inserted into the trachea via a surgical incision in the neck. After insertion of the tube into the trachea, a portion of tube remains outside the patient. This portion extends outwards from the neck and may connect the tracheostomy tube to a ventilator or other medical device. Generally, this exterior portion of the tube is held in place by a flange that rests on the patient's neck and is further secured by straps to the patient. The inserted portion of the tracheostomy tube is generally mechanically coupled to the flange, typically by a snap or screw mechanism on the underside of the flange, which rests on the patient's neck. As such, the mechanical connection point may display angled edges that may irritate a patient's skin. Certain devices attempt to address this problem by providing pillow or fabric protectors for the neck that may lift the flange slightly off the neck to avoid skin irritation. However, these devices may compromise the secure attachment of the tracheostomy tube to the patient by providing a less stable base for the tube at the patient's neck.

A stable attachment of the tracheostomy tube to the patient is advantageous for preventing motion of the tube within the trachea. Because the exterior portion of the tracheostomy tube is connected to the inserted portion, when the exterior portion of the tube is shifted or moved, these movements may be translated to the interior potion of the tube. These movements may cause some discomfort for the patient if the tracheostomy tube shifts position within the trachea.

SUMMARY

Certain aspects commensurate in scope with the originally claimed invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

There is provided a tracheostomy tube that includes a cannula including a distal end and a proximal end, the distal end being adapted to be inserted into a patient's trachea; a flange member molded over the proximal end of the cannula; and a conduit disposed on the flange member in communication with the cannula, wherein the conduit is adapted to operatively connect to a medical device.

There is also provided a method of manufacturing a tracheostomy tube that includes providing a cannula comprising a distal end and a proximal end, the distal end being adapted to be inserted into a patient's trachea; molding a flange member over the proximal end of the cannula such that the proximal end of the cannula is coupled to the flange member; and disposing a conduit disposed on the flange member in communication with the cannula, wherein the conduit is adapted to operatively connect to a medical device.

There is also provided a method of sealing a patient's trachea that includes inserting a tracheostomy tube into a patient's trachea, wherein the tracheostomy tube comprises: a cannula comprising a distal end and a proximal end, the distal end being adapted to be inserted into a patient's trachea; a flange member molded over the proximal end of the cannula; and a conduit disposed on the flange member in communication with the cannula, wherein the conduit is adapted to operatively connect to a medical device.

There is also provided a tracheostomy tube mold form that includes: a mold cavity defining a flange member; a mold cavity defining a conduit adapted to be disposed on the flange member in communication with the cannula; and an opening in the mold form adapted to receive a cannula comprising a distal end and a proximal end, wherein the proximal end of the cannula is adapted to be inserted into at least a portion of the mold cavity defining the flange member.

There is also provided a unitary molded tracheostomy tube assembly that includes: a cannula adapted to be inserted into a patient's trachea comprising a distal end and a proximal end; a flange member disposed on the proximal end of the cannula; and a conduit disposed on the flange member in communication with the cannula, wherein the conduit is adapted to operatively connect to a medical device, and wherein the cannula, the flange member, and the conduit comprise a unitary molded structure.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Provided herein are tracheostomy tubes in which a flange portion is permanently attached to a cannula portion. Such tubes may allow for increased patient comfort. Typical tracheostomy tubes contain a curved cannula portion that is mechanically connected to an outer flange that is designed to rest on a patient's neck. This mechanical connection may include exposed notches or edges that may cause discomfort against a patient's skin. The tracheostomy tubes according to the present techniques may be molded or cast to provide a comfortable coating over the flange/cannula connection point that reduces the chance of such discomfort. Further, the coating results in a more robust tracheostomy tube assembly in which the flange portion is substantially permanently connected to the cannula portion without sacrificing patient comfort for increased durability. In specific embodiments, the tracheostomy tubes may also contain features that reduce the outside forces that may be transferred to inserted portion of the tube, which may cause discomfort if the tube shifts position and contacts the trachea. For example, the exterior flange and other patient exterior assemblies may include regions that allow for flexing or bending of the tracheostomy tube to reduce or eliminate the translation of movement to the interior portion of the tube.

Figures 1A, 2:
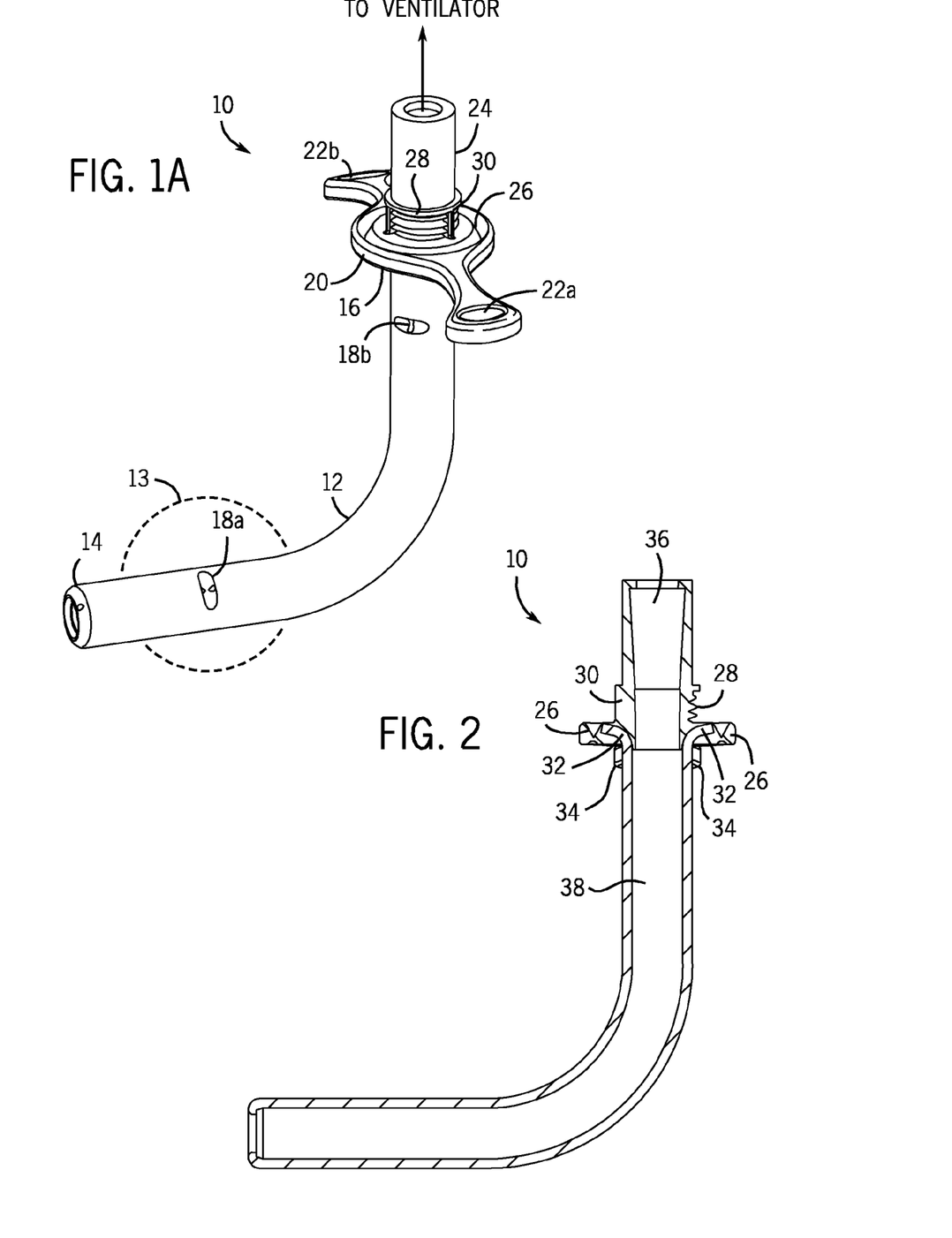
FIG. 2 illustrates a cross-sectional view of the tracheostomy tube of FIG. 1.
Figure 1B:
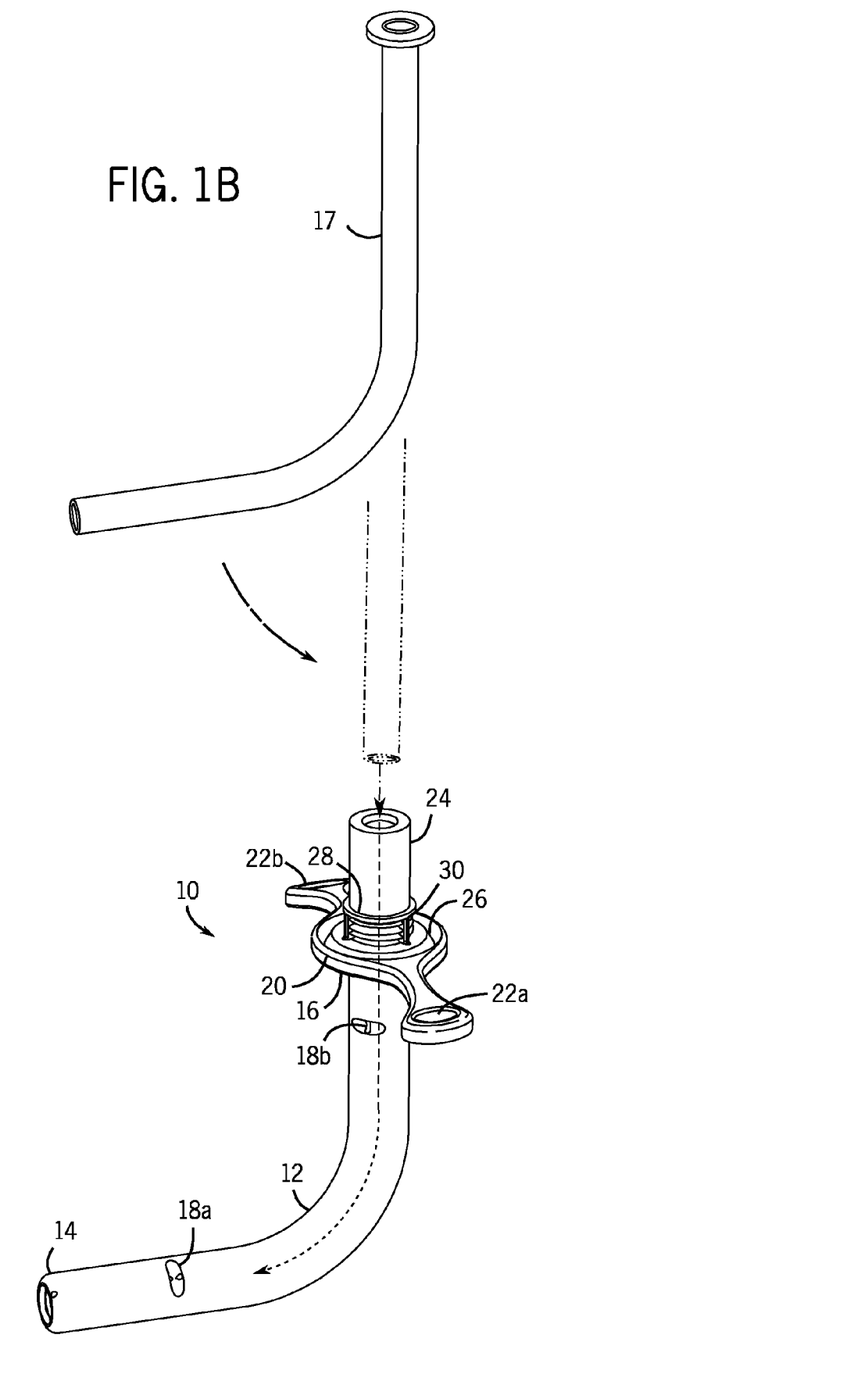
FIG. 1 illustrates a side perspective view of an overmolded tracheostomy tube with bellows and a notched flange in accordance with aspects of the present technique.

FIGS. 1A and 1B show a side perspective view of an exemplary overmolded tracheostomy tube assembly 10 according to the present techniques. In the depicted embodiment, a portion of a cannula 12 is permanently embedded in a portion of a flange 20 member through an overmolding technique, described in detail below. Generally, a region of a preformed cannula 12 may be inserted into a mold suitably sized and shaped to form the flange member 20. A flange material may be injected into the mold so that as the flange material cools and hardens around the cannula 12, it permanently attaches itself to any portion of the cannula 12 that is contained in the mold. Alternatively, as provided herein, a tracheostomy tube assembly 10 may be formed from a single mold. In any case, a flange member 20 may be permanently attached to a cannula 12, without employing a mechanical coupling, such as a snap or screw.

The tracheostomy tube assembly 10 may include an arcuate cannula 12 having a distal end 14, which is generally sized and configured to be inserted through a patient tracheostomy. When the tracheostomy tube assembly 10 is in use, the distal end 14 as well as the major portion of the length of the cannula 12 will reside within the trachea, with the proximal end 16 being generally flush with the anterior surface of the patient's neck. The cannula 12 may also feature a small lumen (not shown) within the wall, accessed by notches 18a and 18b. This lumen is an airway that may be used to fill a balloon type sealing cuff 13 at the patient insertion end. The cuff 13 may be a urethane balloon bonded to the exterior of the cannula 12 such that the notch 18b is encompassed. A user may inject air into the lumen through its access point at notch 18a, which transfers air to the cuff. The cuff 13 may inflate within the patient airway to provide an additional seal.

The tracheostomy tube assembly 10 also features a flange 20 connected to the proximal end 16 of the cannula 12. The flange 20 is designed to rest on the neck of a patient and may feature openings 22a and 22b designed to accommodate attachment straps that may further secure the tracheostomy tube assembly 10 to the neck. The flange 20 may feature a conduit 24 that is substantially in-line with the proximal end 16 of the cannula 12. Generally, the conduit 24 may be adapted to connect the tracheostomy tube 10 to any suitable medical device. For example, the conduit 24 may serve as an insertion point for a disposable cannula lining 17 (shown in FIG. 1B) or may be suitably sized and shaped to connect the tracheostomy tube 10 via medical tubing or other devices to a mechanical ventilator.

In certain embodiments, the flange 20 may include features that allow the conduit 24 to move or flex to accommodate outside forces. Because the conduit 24 may be manipulated by healthcare providers to attach or detach a medical device, it may be advantageous for the conduit 24 to have some freedom of movement. For example, if a healthcare worker exerts force on the conduit 24 to connect a medical device, the conduit 24 may transmit some of that force into a bending or flexing motion so that the cannula 12, which is mostly inside the patient's trachea, does not experience the full force exerted on the conduit 24. As such, the cannula's 12 movements may be reduced, which may result in less irritation of the tracheal walls. Additionally, a flexible medical device connection point, i.e. the conduit 24, may increase possible patient room layout options. Such a feature may be advantageous in emergency room or operating room settings, where larger medical devices may be difficult and time-consuming to move. As depicted in FIG. 1, an annular notch or recess 26 that substantially surrounds the conduit 24 may allow the conduit 24 to have flexibility in several directions. Further, the conduit 24 may also feature a grooved region 28 that may allow additional degrees of freedom to the conduit 24. In certain embodiments, the grooved region 28 may include support ribs 30 to assist in supporting the conduit 24 in a substantially orthogonal position relative to the flange 20 absent any deforming forces applied to the conduit 24.

FIG. 2 is a cross-section view of the tracheostomy tube 10 of FIG. 1. As depicted, a flared portion 32 of the proximal end 16 of the cannula 12 is embedded in the flange member 20. The flange member 20 may also include guides 34 that may provide additional support to the proximal end 16 of the cannula 12. The conduit 24 defines a passageway 36 into which respiratory gases may flow. Passageway 36 may be connected with a passageway 38, defined by the cannula 12, to allow flow of respiratory gases into the trachea. Although the conduit 24 may bend or flex, the passageway 36 will remain substantially in-line with the passageway 38.

The grooved region 28 may include grooves with a substantially V-shaped cross-section with sloping sides that meet in a point, as shown. In other embodiments, the grooves in the grooved region 28 may have different configurations. For example, the grooves may include non-sloping sides that are connected by a substantially flat bottom region. In any case, the grooved region 28 allows the conduit 24 to bend at the area that includes the grooves. Further, in certain embodiments, the grooved region 28 may include semi-annular grooves that may allow flexibility only in certain directions where the grooves are located. Similarly, the notch 26 may also include any suitably shaped annular or semi-annular notch or groove that allows the flange to bend in the area surrounding the conduit.

Figure 3:
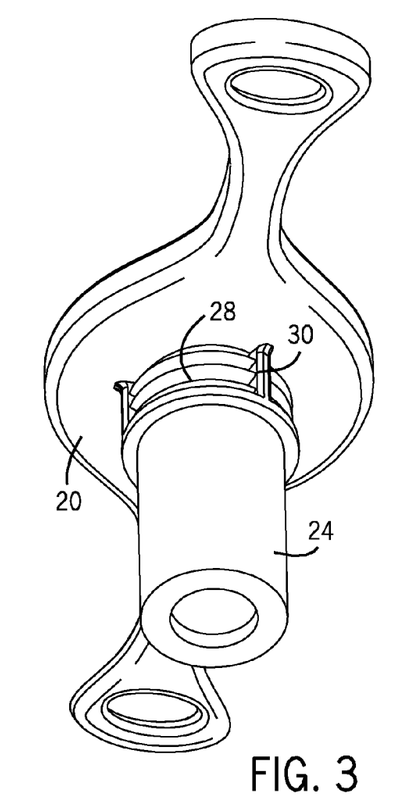
FIG. 3 illustrates an alternative configuration of a flange according to the present techniques.
Figure 4:
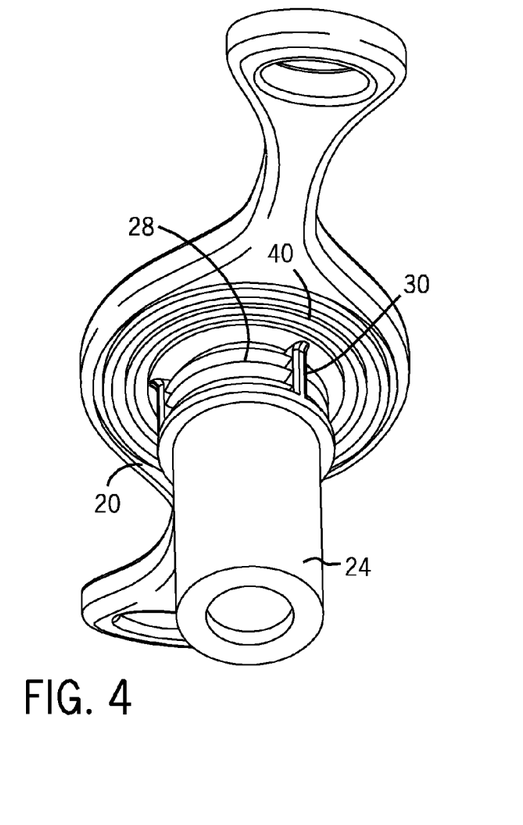
FIG. 4 illustrates another alternative configuration of a flange according to the present techniques.

The flexibility of the conduit 24 may be altered according to the needs of the patient or healthcare workers by altering the configuration of the flange member 20. For example, the flange member 20 illustrated in FIG. 3 includes a grooved region 28 with support ribs 30 without a notch 26 surrounding the conduit 24. Such a configuration may provide increased support to a heavier or larger conduit 24, which may be appropriate for a larger patient, while maintaining some degree of flexibility. The flange member 20 depicted in FIG. 4 includes a grooved region 40 substantially surrounding the conduit 24. Such an embodiment may confer increased degrees of freedom to the conduit 24, which may be advantageous for an active patient. In other embodiments (not shown), a grooved region (e.g. 28 or 40) may contain more or fewer grooves in order to alter the flexibility characteristics of the conduit 24. In other embodiments, a flange member 20 may contain no flexibility features, such as grooves or notches, if a healthcare worker is not particularly concerned about outside forces being transmitted to the tracheal walls. The flange member 20 may also include a certain degree of flexibility through the choice of an appropriate mold material, such as a thermoplastic elastomer. Such an embodiment may be appropriate for a stable patient in an intensive care setting, where the patient is not being moved very often.

Figure 5:
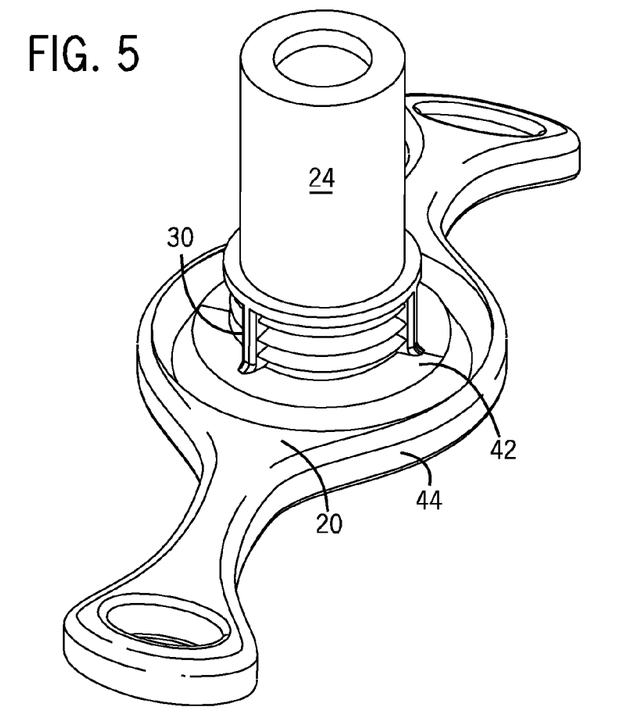
FIG. 5 illustrates yet another alternative configuration of a flange according to the present techniques.

In addition, as depicted in FIG. 5, increased flexibility for the conduit 24 may be achieved by molding portions of the flange member 20 into thin or membranous regions of thermoplastic material, such as a membranous region 42 surrounding the conduit 24. Such flexible regions may allow a greater range of motion for the conduit 24. In certain embodiments, the membranous region may be 0.03-0.05 inches in thickness, while the outer rim 44 of the flange member may be 0.1"-0.2" thick. In an alternative embodiment the conduit 24 may exhibit an outer wall thickness of 0.07"-0.11" be internally ribbed and may include ribs or grooves (not shown) molded into the interior passageway. The support ribs 30, may be 0.03"-0.1" inches in thickness depending on material flexural modulus and may, for example, vary in number from 3 to 6.

Figure 6:
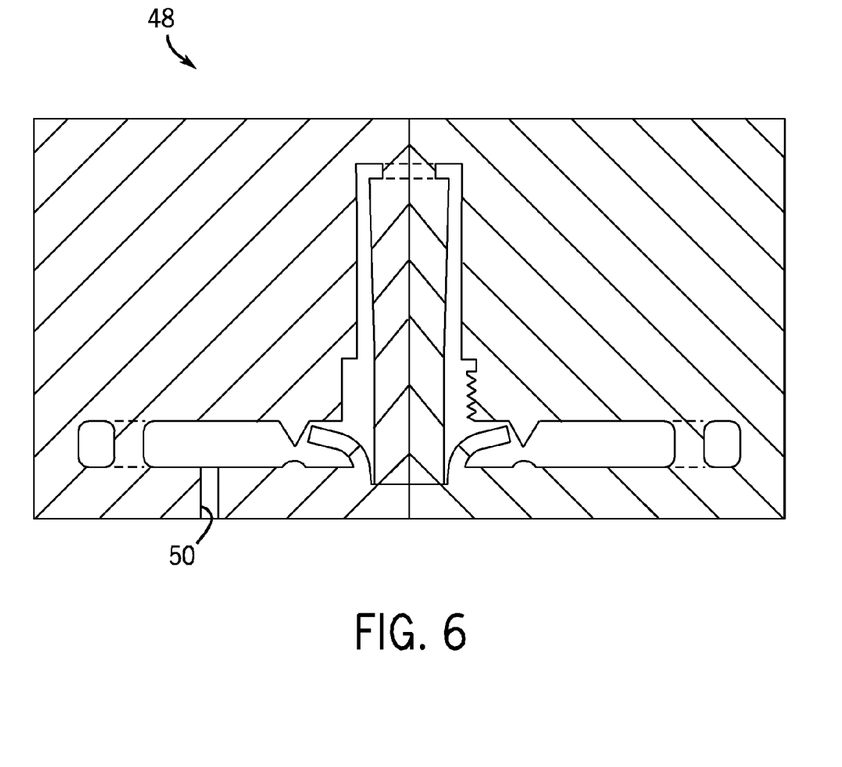
FIG. 6 illustrates an exemplary flange mold according to the present techniques.

The proximal end 16 of the cannula 12 may include a region that is embedded in the flange member 20 through an overmolding process. As noted above, in certain embodiments of the present technique, the tracheostomy tube 10 is overmolded to form a unitary or integral assembly in which the cannula 12 is integrated into the flange member 20 during the manufacturing process. Such overmolded embodiments may result in an assembly in which the tracheostomy tube 10 is completely or partially coated with a thermoplastic material, discussed in more detail herein. For example, the flange member 20 and conduit 24 may be formed by an injection molding process. In one example of such a process, the proximal end 16 of the cannula 12 may be positioned within a die or mold 48, shown in FIG. 6 of the desired shape for the flange member 20 and conduit 24. In certain embodiments, the mold 48 may include cavities defining the guides 34 on either side of an opening in the mold 48 designed to accommodate the proximal end 16 of the cannula 12. The mold 48 may also include an opening 50 into which the mold material may be injected. The guides 34 may help properly position the proximal end 16 of the cannula 12 in the mold. Additionally, the tracheostomy tube 10 may also include a second or distal conduit extension (not shown) that may be inserted into the proximal end 16 of the cannula 12 and radio-frequency welded to the cannula 12.

In certain embodiments, the tracheostomy tube 10 may be constructed, in whole or in part, from polymeric materials, such as thermoplastics, capable of providing a suitable rigidity or semi-rigidity. Examples of such suitable materials include polyvinylchloride, polyurethane, polypropylene and silicone, though other polymeric materials may also be suitable. In one implementation, the overmolding or coating is a thermoplastic elastomer or other conformable coating or material. In such embodiments, the thermoplastic elastomer may include compositions such as styrenic block copolymers, thermoplastic vulcanizate alloys, silicone, thermoplastic polyurethane, and so forth. Further, many elastomer alloys may be suitable as well. As will be appreciated by those of ordinary skill in the art, the overmolding composition may vary, depending on the varying degrees of conformability, durability, wettability, elasticity, or other physical and/or chemical traits that are desired. For example, in certain embodiments, the thermoplastic elastomer is selected to have a hardness between 30 and 60 Shore A to provide a robust yet comfortable material to rest against a patient's skin. In one embodiment, a suitable material having a hardness between 30 and 60 Shore A is employed to mold the flange member 20 while another material having a hardness between between 50 and 70 Shore A is employed to form the cannula 12. In embodiments in which the flange member 20 and the cannula 12 are formed from different materials, these materials may be selected based upon the desirability of a chemical bond between the between the flange member 20 and the cannula 12.

A molten or otherwise unset overmold material may then be injected into the die or mold. For example, in one implementation, a molten thermoplastic elastomer at between about 340° F. to about 430° F. is injected into the mold. The overmold material may then be set, such as by cooling for a period based upon wall thickness where cooling may take place at 30 seconds per 0.100" thickness of overmold material to form the tracheostomy tube 10. In certain embodiments, shear-dependent overmold materials may be advantageous for molding thin or more intricate parts.

In an alternative embodiment, the tracheostomy tube 10 may be formed from a two-shot injection molding process in which a mold is moved or rotated from one injection barrel to a second injection barrel to allow two materials, which may be the same or different, to be injected one after the other in the same mold. Such a process may allow a first molded part to cool before the second molded part is formed. In certain embodiments, the mold may not move or rotate, but movable components within the mold may allow for molding shots from different barrels. In one embodiment, a two-shot molding process may involve injecting a higher durometer material for the conduit and injecting a softer durometer material for the flange. Additionally, insert injection molding techniques may also be appropriate for forming the tracheostomy tube 10.

The cannula 12 may be a pre-formed assembly that may be molded into the appropriate curved configuration or may be extruded and curved into a "J" shape with heat-setting. The proximal end of the cannula 12 may be flared using radio frequency energy. In certain embodiments, it may be advantageous to form perforation or depressions (not shown) into the flared region 32 of the cannula 12. In such an embodiment, the overmolding material may flow into the perforations or depressions to create an improved bond with the flared region 32.

The tracheostomy tubes 10 of the present techniques may be incorporated into systems that facilitate positive pressure ventilation of a patient, such as a ventilator. Such systems may typically include connective tubing, a gas source, a monitor, and/or a controller. The controller may be a digital controller, a computer, an electromechanical programmable controller, or any other control system.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A tracheostomy tube comprising:
a cannula comprising a distal end and a proximal end, the proximal end having a flared portion and the distal end being adapted to be inserted into a patient's trachea;
a flange member molded over the flared portion of the proximal end of the cannula, the flange member having an elongated shape being adapted to support the tracheostomy tube via contact with the patient's neck to maintain the flange member outside of the patient's trachea;
a conduit disposed on the flange member in communication with the cannula, wherein the conduit is adapted to operatively connect to a medical device; and
wherein the flange member comprises at least one groove adapted to allow the conduit to flex relative to the flange member.

2. The tracheostomy tube of claim 1, comprising an inflatable cuff disposed on cannula.

3. The tracheostomy tube of claim 1, wherein the medical device comprises a ventilator.

4. The tracheostomy tube of claim 1, comprising a disposable cannula lining adapted to be slidably insertable into the cannula.

5. The tracheostomy tube of claim 1, wherein the conduit comprises a grooved portion adapted to allow the conduit to flex relative to the flange member.

6. The tracheostomy tube of claim 1, wherein the conduit is adapted to be substantially orthogonal relative to the flange member absent any deforming forces.

7. The tracheostomy tube of claim 1, wherein the flange member comprises a flexible radial section substantially surrounding the conduit adapted to allow the conduit to flex relative to the flange member.

8. The tracheostomy tube of claim 1, wherein the flange member comprises a thermoplastic elastomer, a polyvinylchloride, or a polyurethane.

9. The tracheostomy tube of claim 8, wherein the thermoplastic elastomer comprises at least one of a styrenic block copolymer, thermoplastic vulcanizate alloy, thermoplastic polyurethane, silicone, ethyl vinyl acetate, elastomer alloy, or a combination thereof.

10. The tracheostomy tube of claim 1, wherein the flared region comprises a plurality of perforations.

11. The tracheostomy tube of claim 1, wherein the conduit is integral with the flange member.

12. The tracheostomy tube of claim 1, wherein the flange member is permanently coupled to the proximal end of the cannula.

13. The tracheostomy tube of claim 1, wherein the flange member is chemically bonded to the proximal end of the cannula.

14. A method of manufacturing a tracheostomy tube comprising:
providing a cannula comprising a distal end and a proximal end, the proximal end having a flared portion and the distal end being adapted to be inserted into a patient's trachea;
molding a flange member over the flared portion of the proximal end of the cannula, the flange member having an elongated shape being adapted to support the tracheostomy tube via contact with the patient's neck to maintain the flange member outside of the patient's trachea;
disposing a conduit on the flange member in communication with the cannula, wherein the conduit is adapted to operatively connect to a medical device; and
providing at least one groove on the flange member adapted to allow the conduit to flex relative to the flange member.

15. The method of claim 14, comprising disposing an inflatable cuff on the cannula.

16. The method of claim 14, comprising providing a disposable cannula lining adapted to be slidably insertable into the cannula.

17. The method of claim 14, comprising molding a grooved portion on the conduit adapted to allow the conduit to flex relative to the flange member.

18. The method of claim 14, wherein disposing the conduit comprises molding the conduit along with the flange member.

19. The method of claim 14, comprising providing a flexible radial section on the flange member substantially surrounding the conduit adapted to allow the conduit to flex relative to the flange member.

20. The method of claim 14, wherein the flange member is molded over the proximal end of the cannula by injection molding, insert injection molding, or two-shot molding.

21. The method of claim 14, comprising providing a second conduit extending from the conduit.

22. The method of claim 14, wherein the flared region comprises a plurality of perforations.

23. A method of sealing a patient's trachea comprising:
inserting a tracheostomy tube into the patient's trachea, wherein the tracheostomy tube comprises:
a cannula comprising a distal end and a proximal end, the proximal end having a flared portion and the distal end being adapted to be inserted into the patient's trachea;
a flange member molded over the flared portion of the proximal end of the cannula, the flange member having an elongated shape being adapted to support the tracheostomy tube via contact with the patient's neck to maintain the flange member outside of the patient's trachea;
a conduit disposed on the flange member in communication with the cannula, wherein the conduit is adapted to operatively connect to a medical device; and
wherein the flange member comprises at least one groove adapted to allow the conduit to flex relative to the flange member.

24. The method of claim 23, comprising inflating a cuff disposed on cannula.

25. The method of claim 23, wherein the medical device comprises a ventilator.

26. The method of claim 23, comprising inserting a disposable cannula lining into the cannula.

27. The method of claim 23, wherein the conduit comprises a grooved portion adapted to allow the conduit to flex relative to the flange member.

28. The method of claim 23, wherein the flange member comprises a flexible radial section substantially surrounding the conduit adapted to allow the conduit to flex relative to the flange member.

29. A method of sealing a patient's trachea comprising:
inserting a tracheostomy tube into the patient's trachea, wherein the tracheostomy tube comprises:
a cannula comprising a distal end and a proximal end, the proximal end having a flared portion and the distal end being adapted to be inserted into the patient's trachea, wherein the proximal end of the cannula comprises a flared region and the flared region comprises a plurality of perforations;
a flange member molded over the flared portion of the proximal end of the cannula, the flange member having an elongated shape being adapted to support the tracheostomy tube via contact with the patient's neck to maintain the flange member outside of the patient's trachea;
a conduit disposed on the flange member in communication with the cannula, wherein the conduit is adapted to operatively connect to a medical device; and
wherein the flange member comprises at least one groove adapted to allow the conduit to flex relative to the flange member.

30. A unitary molded tracheostomy tube assembly comprising:
a cannula adapted to be inserted into a patient's trachea comprising a distal end and a proximal end;
a flange member disposed on a flared proximal end of the cannula, the flange member having an elongated shape being adapted to support the tracheostomy tube via contact with the patient's neck to maintain the flange member outside of the patient's trachea;
a conduit disposed on the flange member in communication with the cannula, wherein the conduit is adapted to operatively connect to a medical device, wherein the cannula, the flange member, and the conduit comprise a unitary molded structure; and
wherein the flange member comprises at least one groove adapted to allow the conduit to flex relative to the flange member.

31. A tracheostomy tube, comprising:
a cannula having a distal end and a proximal end, the distal end of the cannula being configured to be inserted into a trachea;
a conduit having a first passageway being communicatively coupled to the proximal end of the cannula, the conduit being configured to attach to an external medical device; and
a flange member having one or more grooved regions configured to allow the conduit to flex relative to the flange member and one or more support ribs configured to maintain the conduit in a substantially orthogonal position relative to the flange member, the flange member being adapted to support the tracheostomy tube via contact with a patient's neck to maintain the flange member outside of the trachea.

32. The tracheostomy tube of claim 31, wherein the flange member is permanently attached to the cannula via injection molding, insert injection molding, or two-shot molding.

33. The tracheostomy tube of claim 31, wherein the external medical device comprises at least one of a mechanical ventilator, medical tubing, a medical sensor, or a computer, or any combination thereof.

34. The tracheostomy tube of claim 31, comprising a cannula lining configured to be removably inserted into the cannula.

* * * * *